United States Patent
Michiels et al.

(10) Patent No.: US 6,780,887 B1
(45) Date of Patent: Aug. 24, 2004

(54) ANTI-ISCHEMIC COMPOUNDS

(75) Inventors: Carine Michiels, Spy (BE); Martine Redon, Namur (BE); Jose Remacle, Malonne (BE)

(73) Assignee: Societe de Conseils de Recherches et d'Applications Scientifiques (S.C.R.A.S.), Paris (FR)

( * ) Notice: Subject to any disclaimer, the term of this patent is extended or adjusted under 35 U.S.C. 154(b) by 54 days.

(21) Appl. No.: 10/110,662

(22) PCT Filed: Oct. 11, 2000

(86) PCT No.: PCT/EP00/10085

§ 371 (c)(1), (2), (4) Date: Jul. 30, 2002

(87) PCT Pub. No.: WO01/28549

PCT Pub. Date: Apr. 26, 2001

(30) Foreign Application Priority Data

Oct. 15, 1999 (EP) .......................... 99870212

(51) Int. Cl.[7] .............................. A61K 31/35
(52) U.S. Cl. ................ 514/456; 514/300; 514/301; 514/302; 514/421; 514/457; 514/464; 514/465; 549/283; 549/285; 549/305; 549/306; 548/453; 546/113; 546/114; 546/115; 546/183
(58) Field of Search .................. 549/283, 285, 549/305, 306; 548/453; 546/113, 114, 115, 183; 514/300, 301, 302, 421, 457, 465, 456, 464

(56) References Cited

FOREIGN PATENT DOCUMENTS

| | | |
|---|---|---|
| EP | 0099091 | 1/1984 |
| FR | 2539412 | 7/1984 |
| WO | WO 87/05898 | 10/1987 |
| WO | WO 97/16184 | 5/1997 |
| WO | WO 99/37294 | 7/1999 |

OTHER PUBLICATIONS

Ukrainets, I.V., et al. (1994) *Ethyl Esters of Malonanilic Acids. Synthesis and Pyrolysis.* Tetrahedron 50(34):10331–10338.

Venuti, M.C., et al. (1988) *Inhibitors of Cyclic AMP Phosphodiesterase. 4. Synthesis and Evaluation of Potential Prodrugs of Lixazinone.* J. Med. Chem. 31:2145–2152.

Oumar–Mahamat, H., et al. (1989) *Mn (III)–mediated Radical Lactonisation of Allylic Esters of Acetoacetic and Malonic Acids.* Tetrahedron Letters 30(3): 331–332.

Hollowood, J., et al. (Sep. 1967) *Local Anesthetics with Enhanced Affinity for Proteins.* Local Anesthetics 863–867.

McLaughlin, B.A., et al. (1998) *Toxicity of Dopamine to Striatal Neurons In Vitro and Potentiation of Cell Death by a Mitochondrial Inhibitor.* J. Neurochemistry 70(6):2406–2415.

*Primary Examiner*—Amelia A. Owens
(74) *Attorney, Agent, or Firm*—Knobbe, Martens, Olson & Bear LLP

(57) ABSTRACT

The present invention is related to a compound of formula (I), salts and pro-drugs of the compound (I) and methods for treating and/or preventing partial or total ischemia, methods for treating and/or preventing pathologies associated with ischemia or with mitochondrial deficiencies.

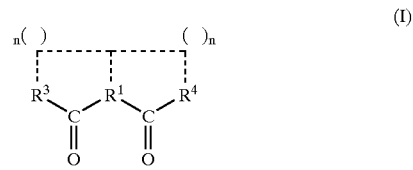

n = 1, 2

18 Claims, No Drawings

ANTI-ISCHEMIC COMPOUNDS

RELATED APPLICATION DATA

This application is a National Phase application under 35 U.S.C. §371 of International Application Number PCT/EP00/10085, filed Oct. 11, 2000 which claims priority to European Application Number 99870212.0 filed Oct. 15, 1999.

OBJECT OF THE INVENTION

The present invention relates to new therapeutic agents with a protective effect on proteinic complexes of the inner mitochondrial membrane and that can be used preferably for preventing and/or treating partial or total ischemia, pathologies associated with ischemia or associated with mitochondrial deficiencies, or apoptosis.

INVENTION-BASED TECHNOLOGICAL BACKGROUND

Ischemia is an interruption of the blood irrigation of an organ or a tissue through artery obliteration, compression or spasma. The consequences depend on the nature of the tissue being deprived of oxygenated blood and the phenomenon duration. Total ischemia leads to tissue necrosis in a period of time variable according to the oxygen needs. Partial ischemia causes either a reduction of the organ capabilities (psychic slowing down, hepatic or kidney function insufficiency, etc.) or the incapability to modify its work at any stimulation, showing then signs of pain (angina pectoris crises, arteritis cramps). Ischemia is very deleterious for the nerve tissue. It is first to be seen in reversible metabolic and functional troubles that can lead to an abnormal nervous activity, for example, an epilepsy crisis or some cerebral cortex ischemic lesions. After a few minutes of ischemia, irreversible lesions of the nervous tissue appear, accompanied with cellular body swelling followed by necrosis thereof. This is called cerebral infarction.

It is known to use agonist molecules for alpha-adrenergic receptors and agonist molecules for alpha-pre-synaptic receptors for treating ischemia. Such compounds are used at the heart level for treating angor, which is a clinical expression of acute myocardial ischemia and the result of a temporary imbalance between the myocardium oxygen demand and the oxygen intake through circulation, leading possibly, in serious cases, to a myocardial infarction.

STATE OF THE ART

The use of various plant extracts for treating and/or preventing ischemia or pathologies associated with ischemia or an energy deficiency is described in International Patent Application WO 98/51291. This document also describes the working mechanism of said molecules that allow an inhibition of the activation cascade of the endothelial cells induced by hypoxia as well as the protective effect of such products on some mitochondrial deficiencies, particularly with a protective effect of the mitochondria complexes I and III. This document gives a biochemical model making it possible to obtain in vitro a protective effect from anti-ischemic compounds.

The Publication by Ukrainets I. et al. (*Tetrahedron Letters* Vol. 50, n° 34, p. 10331–10338 (1994)) describes derivatives and the malonic acid synthesis, particularly an ethyl malonic acid ester and symmetrical diamylides.

Malonic acid derivatives and their use for delaying plant growth are described in International Patent Application WO 87/05898.

The Publication by Venuti et al. (*J. of Med. Chem.* Vol. 31, p. 2145–2152 (1988)) describes, by way of an intermediate compound, a malonic acid derivate involved in the synthesis of compounds being used as prodrugs.

The Publication by Oumar-Mahamat et al. (*Tetrahedron Letters* Vol. 30, n° 3, p. 331–332 (1989)) describes cyclic malonic acid derivates.

Patent Application EP-A-0,099,091 describes hexahydrodioxypyrimidine derivates, the production method thereof and their use as antiviral, anti-bacterial and antitumor compounds.

Patent Application FR-2,539,412 describes 5-fluorouracyl derivates and their therapeutic use as carcinostatic agents.

The Publication by Holwood et al. (*J. of Med. Chem.* Vol. 10, n° 5, p. 863–867 (1967)) describes as local anesthetics, various derivates, more particularly 2-ethoxycarbonyl-aceto-2',6'-xylide or its corresponding amide.

The Publication by McLaughlin et al. (*J. of Neurochem.* Vol. 70, p. 2406–2415 (1998)) describes the effect of dopamine on the mitochbndrial inhibition compared to that of methylmalonate.

Patent Application WO97/16184 describes methods for treating ischemia comprising the step of administrating an acyl-co-enzyme A cholesterol O acyltransferase (ACAT) inhibitor such as dodecyl N-(2,6-diisopropylphenyl)-2-phenyl-malomanic acid ester and a HMG-co-enzyme A reductase inhibitor.

AIMS OF THE INVENTION

The aim of the present invention is to provide new compounds designed to induce a protective effect on protein complexes of the inner mitochondrial membrane and designed to be used particularly for preventing or treating partial or total ischemia, pathologies associated with ischemia or pathologies associated with mitochondrial deficiencies.

A particular aim of the present invention is to provide compounds with an improved activity and/or with no side effects of molecules in the state of the art.

CHARACTERISTIC ELEMENTS OF THE INVENTION

The present invention relates particularly to new compounds of formula I, the salts thereof and prodrugs of such compounds:

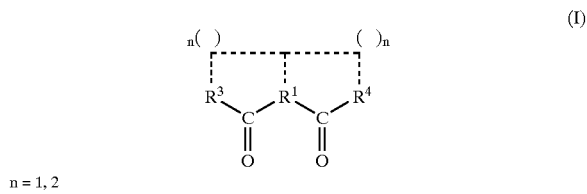

wherein:

$R^1$ is $CH_2$, NH or a ligand, preferably a carbon atom, forming together with $R^3$ and/or $R^4$ an aromatic or non-aromatic ring having 5 or 6 carbon atoms (n=1 or 2), optionally comprising on each ring an heteroatom, preferably a nitrogen, oxygen or sulfur atom;

$R^3$ and/or $R^4$ represent:

an amine with the formula:

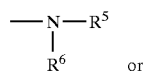

a group having the formula $—Z—R^6$ wherein:

Z represents O or S, $R^5$ represents H or an alkyl group with 1 to 6 carbon atoms (preferably, $R^5$ represents a methyl or ethyl group), $R^6$ represents an hydrophobic group, preferably selected amongst the group consisting of a tert-butyl group, an allyl group or a (aromatic or non aromatic) ring having 5, 6 or 7 carbon atoms optionally comprising one or more heteroatoms (preferably N, O or S) and wherein the carbon atoms are optionally substituted for by:

an alkyl group $R^7$ having 1 to 6 carbon atoms (preferably, a methyl or ethyl group), a ketone group, a hydroxyl group, an ester group, a halogen element (F, Cl, Br or I), a trifluoromethyl ($CF_3$) group, or a group having the formula:

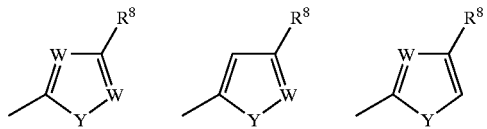

wherein:

W represents CH or a nitrogen atom,

Y represents S or O, and $R^8$ represents an alkyl group having 1 to 6 carbon atoms (preferably a methyl or ethyl group), with the additional condition that, if $R^3$ forms together with $R^1$ said above-mentioned ring or if $R^3$ is either an amine of formula:

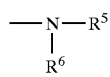

$R^4$ represents an alkyl group (preferably a propene) having 1 to 10 (preferably 1 to 6) carbon atoms, either saturated or unsaturated, optionally comprising one or more heteroatoms (preferably N, S or O). Additionally, in said alkyl group, one or more carbons can optionally be substituted for by an halogen element (fluorine, chlorine, bromine or iodine) or a trifluoromethyl group (CF3).

In the compounds having formula I, $R^3$ and $R^4$ preferably represent an amine having the formula:

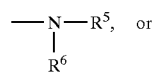

a group having the formula $—Z—R^6$ wherein $R^5$ represents H or a methyl group, Z represents O or S (preferably O) and $R^6$ represents a cyclopentene, a cyclohexane or a benzene group.

According to the invention, are excluded as compounds already described in the state of the art, compounds having the formula I wherein $R^1$ is $CH_2$, $R^3$ is a compound having the formula $Z—R^6$ wherein Z represents O, $R^6$ represents an ethyl group, $R^3$ is an amine having the formula $NH—R^{6'}$ wherein $R^{6'}$ represents a cyclic compound (optionally 2-substituted with an hydroxyl group) and compounds having formula I wherein $R^1$ is $CH_2$, $R^3$ and $R^4$ are amines having the formula $NH—R^6$ wherein $R^6$ represents a ring having 6 carbon atoms 2-substituted by an hydroxyl group.

Also excluded from the invention, as already described compounds, are the compounds described in tables 1, 2, and A in the Application WO87/05898, the dodecyl N-(2,6-diisopropylphenyl)-2-phenyl-malonamic acid ester and the compound having the formula I wherein $R^1$ is $CH_2$, $R^4$ is a group having the formula $Z—R^6$ (Z represents oxygen and $R^6$ represents an alkyl group) and wherein $R^3$ is an amine of formula II:

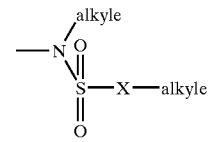

wherein X represents O, S, $CH_2$ or C=O and derivatives having formula:

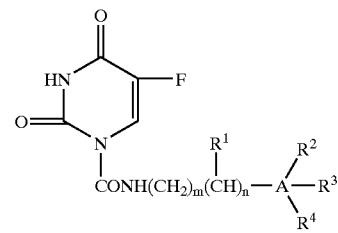

wherein $R^1$ represents a $C_1–C_6$ alkyl group, A represents a saturated or unsaturated ring having 3 to 7 carbon atoms; each of $R^2$, $R^3$ and $R^4$ represents, independently, a hydrogen or halogen atom or a group such as $C_1–C_6$ alkoxy, $C_1–C_6$ alkyl, $C_1–C_6$ alkylthio, $C_1–C_6$ alkoxy-carbonyl, carboxyl, carboxamido, sulfonic acid, sulfonamido, acylamino, sulfonylamino, $C_1–C_6$ alkylsulfonyle, nitrile, nitro, acyloxy, phenyl or methylene-dioxy groups and each of m and n represents an integer from 0 to 4.

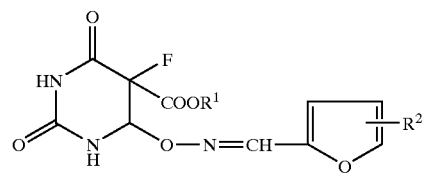

wherein:

$R^1$ represents an alkyl group, $R^2$ is hydrogen or an alkyl group.

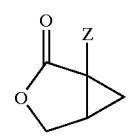

wherein Z=CO methyl, COO methyl, or COO alkyl

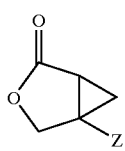

$Z=CO_2CH_3, CO_2C_2H_3$ or $CO_2H$

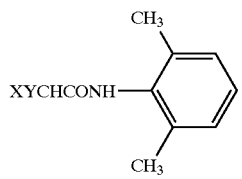

wherein X=CON H and Y=H.

According to the invention, the aromatic or non aromatic rings optionally comprise one or more heteroatoms, preferably one or more oxygen or sulfur atoms, and wherein the carbon atoms are substituted for either by ketone, hydroxyl or ester groups or by an halogen element such as described above.

The preferred compounds according to the invention are selected from the group comprised of dicyclopenten-2-yl malonate, 2-propenyl-3-oxa-2-oxobicylo[3.1.0]hexane-1-carboxylate, ethylcyclopenten-2-yl malonate, methylcyclopenten-2-yl malonate, N,N'-diphenyl malonamide, ethyl-N-phenylamido ethanoate, ethyl-2,6-dimethyl-N-phenylamido ethanoate, ethyl-N-methyl-N-cyclohexylamido ethanoate and dicyclopentene-2-yl malonate, optionally their salts or prodrugs thereof.

The present invention also relates to pharmaceutically acceptable non-toxic acid addition salts of compounds according to the invention having an amine. Examples of pharmaceutically acceptable acids may include mineral acids, such as hydrochloric, hydrobromic, sulfuric, nitric, phosphoric acids, etc. and organic acids such as. acetic, citric, tartaric, benzoic, salicylic, maleic acids, etc.

The present invention also relates to the first application of compounds having formula I as a drug, as well as their salts and prodrugs of said compounds, except for the following known compounds: the N-(2,6-diisopropyl-phenyl)-2-phenyl-malonamic acid dodecyl ester and the compounds having formula I wherein $R^1$ is $CH_2$, $R^4$ is a group having formula $Z—R^6$ wherein Z represents oxygen and $R^6$ represents an alkyl group and wherein $R^3$ is an amine of formula II:

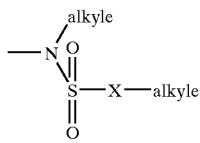

wherein X represents O, S, $CH_2$ or C=O and the derivatives having formula:

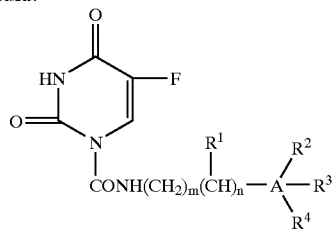

wherein $R^1$ represents a $C_1$–$C_6$ alkyl group, A represents a saturated or an unsaturated ring having 3 to 7 carbon atoms;

each of $R^2$, $R^3$ and $R^4$ represents, independently, a hydrogen or halogen atom, or a group such as $C_1$–$C_6$ alkoxy, $C_1$–$C_6$ alkyl, $C_1$–$C_6$ alkylthio, $C_1$–$C_6$ alkoxycarbonyl, carboxyl, carboxamido, sulfonic acid, sulfonamido, acylamino, sulfonylamino, $C_1$–$C_6$ alkylsulfonyl, nitrile, nitro, acyloxy, phenyl or methylene-dioxy groups and each of m and n represents an integer from 0 to 4.

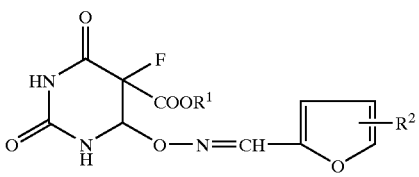

wherein $R^1$ represents an alkyl group, $R^2$ hydrogen or an alkyl group.

According to the invention, it is meant by "prodrugs" functional derivatives of formula I compounds that may be converted, preferably in vivo, in the patient depending on the required formula I form. Such prodrugs of these compounds can be obtained using methods well-known to the man of the art such as those described in the document entitled: "*Design and Prodrugs*", Ed. H. Bundgaard, Elsevier (1985). The compounds according to the invention relate to two enantiomeric forms, the various separate isomers or a mixture thereof.

The new compounds according to the invention are advantageously used in order to obtain a protective effect on the protein complexes of the inner mitochondrial membrane of a mammalian's cells, preferably a human being. The compounds according to the present invention are more particularly applied to prevent and/or treat partial or total ischemia, pathologies associated with ischemia or pathologies associated with mitochondrial deficiencies.

It is meant by "(partial or total) ischemia, pathologies associated with ischemia and pathologies associated with mitochondrial deficiencies", diseases, preferably vascular ones, selected amongst the group consisting of myocardial infarction, cerebral ischemia, chronic veinous insufficiency, arteriopathies, i.e. lesions due to atherosclerosis affecting patients' arteries, more particularly those of the lower limbs, the Raynaud's phenomenon linked to vasospasms, leading to an artery vasoconstriction, ulcers, gangrene, alteration of the capillary permeability, capillary fragility, cicatrizations, skin alterations, retinal defects from ischemic origin, decrease of the auditive acuity from ischemic origin, troubles associated with stays in high altitude regions, angina pectoris caused by short periods of coronary obstruction, pulmonary hypertension, hepatic ischemia, Parkinson disease, myopathies and syndroms associated with vascular problems, such as diabetes, where a hypertension and an alteration of the blood flow appear in the lower limbs. Such pathologies and diseases linked to ischemia are well-known to the clinicians and practitioners who are able to adapt the use of the pharmaceutical composition for treating and/or preventing symptoms and dysfunctions of the human or animal body associated with the above-mentioned diseases and/or for preventing or reducing the possibility of being affected by them.

The Applicants have unexpectedly found out that such various syndroms or diseases can be treated using the compounds of the invention, their optional salts and prodrugs thereof, and that such compounds act according to the same biochemical action mode.

Another aspect of the present invention relates to a pharmaceutical composition comprising an appropriate pharmaceutical carrier or excipient and a sufficient amount of one or more compounds according to the invention, i.e. an amount sufficient to at least improve or prevent the above-mentioned symptoms in a mammalian, more particularly a human being. Such a sufficient amount may vary depending on some factors such as the condition of the animal to be treated, the administration route, the side-effect severity, the compound stability in the circulating serum or blood, etc. Preferably, the compound sufficient amount to be used in the pharmaceutical composition of the invention is in the range between 0.1 and 200 mg/patient, more preferably between 1 and 50 mg/patient, most preferably between 20 and 30 mg/patient, this amount being optionally able to be adapted particularly depending on the necessary administration doses and the patient's weight, as this may be extrapolated from in vivo application examples, as disclosed hereinafter.

The pharmaceutical composition comprises an appropriate pharmaceutical carrier that can vary according to the administration mode and can be possibly combined with an adjuvant, so as to improve the therapeutic properties of the compound according to the invention or to reduce its possible side effects. Such appropriate pharmaceutical carriers or adjuvants are well-known to the man of the art and can be prepared following the procedures generally applied by chemists and may comprise any non toxic pharmaceutical carrier, either solid (including in powder form), liquid (solutions, suspensions, emulsions, etc.) or gaseous. The active pharmaceutical compound percentage (generally in the range between 5% and 70% in weight) may vary depending on the administration frequency and the possible side-effects on animal, including on human being.

In order to prepare such pharmaceutical compositions in the form of tablets, granules, capsules or tablets, suspensions, etc., it is possible to incorporate elements such as corn starch, lactose, sucrose, sorbitol, talcum, stearic acid, magnesium stearate, gums or diluents comprising a variable percentage of water or a solvent such as a syrup, oil or water suspensions, perfumed emulsions, etc. Dispersible agents used in aqueous compositions may comprise gums, alginates, dextrans, carboxymethyl cellulose derivatives, etc.

The present invention also relates to a therapeutic or preventive treatment method for ischema or pathologies associated with ischemia as above-mentioned, which includes administering a sufficient amount of formula I compound or of the pharmaceutical composition of the invention to said patient, preferably a human being, so as to prevent, reduce or eliminate the symptoms of ischemia, of pathologies associated with ischemia or associated with mitochondrial deficiencies, or apoptosis, with the additional condition that the compound is neither the dodecyl N-(2,6-diisopropyl-phenyl-)-2-phenyl-malonamic acid ester nor a formula I compound wherein $R^1$ is $CH_2$, $R^4$ is a group having the formula —Z—$R^6$ wherein Z represents oxygen and $R^6$ represents an alkyl group and wherein $R^3$ is an amine having formula II:

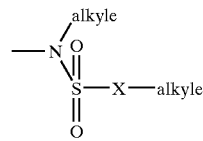

wherein X represents O, S, $CH_2$, C=O.

A last aspect of the present invention relates to using such compounds or the pharmaceutical composition of the invention for preparing a drug for treating or preventing ischemia, pathologies associated with ischemia or associated with mitochondrial deficiencies, such as above-mentioned, or apoptosis, with the additional condition as mentioned in the preceding paragraph.

The present invention also relates to a method for preparing compounds of the invention having formula I, comprising the following steps:
esterification of an intermediate compound $R^3$—H by a group of the following formula:

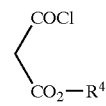

in the presence of dicyclohexyl carbodiimide (DCC),
optionally followed by one or more cyclizing reactions in the presence of an oxidizing agent such as manganese acetate Mn(III) or monohydrate copper acetate Cu(II), and optionally sodium acetate.

The definitions of the above-mentioned moieties are those given in formula I for the compounds of the invention.

The various aspects of the present invention are described more in details in the non limitative examples presented hereinafter.

EXAMPLES

Example 1

Dicyclopenten-2-yl malonate Synthesis
2-Cyclopentenol Synthesis

Such synthesis has been conducted according to the method described by A. L. Gemal and J. L. Luche (J. Am. Chem. Soc. 103, p. 5454 (1981)).

To a 2-cyclopentenone solution (5.00 g; 60.90 mmols) in (commercial, 99%) methanol is added heptahydrate cerium chloride ($CeCl_3.7H_2O$) (22.69 g; 60.90 mmols) and the reaction mixture is stirred at room temperature for 40 minutes for homogeneization. The mixture is then cooled down to 0° C. and sodium borohydride ($NaBH_4$) (2.30 g; 60.90 mmols) is slowly added. After complete addition, the mixture is stirred at 0° C. for 3 hours. A hydrochloric acid diluted solution is then added in order to adjust the pH to 7. The phases are separated and the aqueous phase is extracted several times with ether (5×50 ml). The combined organic phases are dried on anhydrous $MgSO_4$ and concentrated in order to give the 2-cyclopentenol (3.81 g; 74%).

Dicyclopenten-2-yl malonate Synthesis

To a 2-cyclopentenone solution (1.00 g; 11.89 mmols) in 50 ml dichloromethane are successively added malonic acid (1.12 g; 10.81 mmols) and 4-dimethylamino pyridine (DMAP) (0.13 g; 1.08 mmols). The reaction mixture is stirred under inert atmosphere and cooled down to 0° C. At this temperature, dicyclohexyl carbodiimide (DCC) (2.34 g; 11.35 mmols) is added in one single portion. A milky white mixture is obtained, which is stirred at 0° C. for 1 hour, followed by room temperature until complete reaction (reaction evolution monitoring by TLC, eluent pentane/ethyl acetate: 8/2). The precipitate is filtered out on celite and washed with dichloromethane. The filtrate is washed with a $NaHCO_3$ (10 ml) saturated aqueous solution. The phases are separated and the aqueous phase is extracted with dichloromethane (3×10 ml). The combined organic phases are successively washed with a NaCl saturated aqueous solution and water, then dried on anhydrous $MgSO_4$ and concentrated. The precipitate is again filtered out through filtration on celite and washed with pentane. The purification of the reaction raw product is performed by silica column chromatography (elution pentane/ethyl acetate: 8/2) to give MRC2P119 (2.40 g; 94%) in the form of a colourless oil.

Product Characterization $^1$H NMR (CDCl$_3$, 400 MHz)δ: 1.81–2.55 (m, 8H), 3.32 (s, 2H), 5.76–5.84 (m, 4H), 6.12 (m, 2H); $^{13}$C NMR (CDCl$_3$, 175 MHz)δ: 29.05, 30.53, 41.36, 80.97, 128.33, 137.44, 165.92; IR (film): 3,450, 3,062, 2,947, 2,858, 1,727, 1,618, 1,454, 1,411, 1,348, 1,319, 1,270, 1,151, 1,029, 973, 917, 878, 783, 735 cm$^{-1}$; PM: 236.27; MS m/z 171 (M$^+$–65); calculated elementary analysis C (66.09%), H (6.82%); found C (66.09%), H (6.90%).

Example 2

2-propenyl-3-Oxa-2-Oxobicyclo[3.1.0]-hexane-1-carboxylate

Diallyl Malonate Synthesis

To a malonic acid solution (5.00 g; 48.05 mmols) in 330 ml dichloromethane are successively added allyl alcohol (10.51 g; 124.93 mmols) and DMAP (1.17 g; 9.61 mmols). The reaction mixture is stirred under inert atmosphere and cooled down to 0° C. At this temperature, DCC (20.82 g; 100.90 mmols) is added in one single portion. A milky white mixture is obtained, which is stirred at 0° C. for 1 hour, followed by room temperature until complete reaction (reaction evolution monitoring by TLC, eluent pentane/ethyl acetate: 9/1). The precipitate is filtered out on celite and washed with dichloromethane. The filtrate is washed with a NaHCO$_3$ (20 ml) saturated aqueous solution. The phases are separated and the aqueous phase is extracted with dichloromethane (3×20 ml). The combined organic phases are successively washed with a NaCl saturated aqueous solution and water, then dried on anhydrous MgSO$_4$ and concentrated. The precipitate is again filtrated on celite and washed with pentane. The purification is performed by silica column chromatography (elution pentane/ethyl acetate: 9/1) to give the compound of the invention (MRC2PSS) (8.09 g; 92%) in the form of a colourless oil.

Product Characterization $^1$H NMR (CDCl$_3$, 400 MHz)δ: 3.44 (s, 2H), 4.64 (d, J=5.9 Hz, 4H), 5,24 (d, J=10.3 Hz, 2H), 5.34 (d, J=17.1 Hz, 2H), 5.91 (ddt, J=17.1–10.3–5.9 Hz, 2H); $^{13}$C NMR (CDCl$_3$, 175 MHz)δ: 40.99, 65.57, 118.20, 131.26, 165.68; IR (film): 3,653, 3,089, 2,989, 2,951, 1,739, 1,650, 1,450, 1,414, 1,368, 1,330, 1,274, 1,150, 995, 935, 631 cm$^{-1}$; PM: 184.19; MS m/z 184 (M$^{3O}$); calculated elementary analysis C (58.69%), H (6.57%), found C (58.66), H (6.57%).

2-Propenyl-3-oxa-2-oxobicyclo[3.1.0]hexane-1-carboxylate Synthesis

To a diallyl malonate solution (MRC2P55) (2.00 g; 10.86 mmols) in 55 ml icy acetic acid are successively added dihydrate. manganese(III) acetate (Mn(OAc)$_3$.2H$_2$O) (11.64 g; 43.43 mmols), monohydrate copper(II) acetate (Cu(OAc)$_2$.H$_2$O) (4.34 g; 21.72 mmols) and sodium acetate (AcONa) (1.78 g; 21.72 mmoles). The resulting brown solution is heated at 80° C. for 20 hours (this corresponds to the brown coloration disappearance and the appearance of a turquoise blue coloration). The reaction evolution is monitored by TLC (eluent pentane/ethyl acetate: 9/1). The precipitate is filtered out on celite and washed with dichloromethane. The filtrate is washed with water (30 ml). The aqueous phase is extracted with dichloromethane (2×20 ml). The combined organic phases are successively washed with water (2×20 ml) and a NaHCO$_3$ saturated aqueous solution (2×20 ml), then dried on anhydrous MgSO$_4$ and concentrated. The reaction raw product is purified by silica column chromatography (elution pentane/ethyl acetate: 1/1) to give the compound of the invention (MCR2PS7) (0.49 g; 25%) in the form of a colourless oil.

Product Characterization $^1$H NMR (CDCl$_3$, 400 MHz)δ: 1.41 (dd, J=5.4–4.9 Hz, 1H), 2.10 (dd, J=8.0–4.6 Hz, 1H), 2.79 (m, 1H), 4.20 (d, J=9.3 Hz, 1H), 4.38 (dd, J=9.3–4.9 Hz, 1H), 4.68 (d, J=5.4 Hz, 2H), 5.28 (dd, J=10.2–1.5 Hz, 1H), 5.39 (dd, J=17.1–1.5 Hz, 1H), 5.94 (ddt, J=17.1–10.2–5.4 Hz, 1H); $^{13}$C NMR (CDCl$_3$, 175 MHz)δ: 20.56, 27.82, 29.09, 65.97, 66.85, 118.60, 131.10, 166.14, 170.20; IR (film) 3,653, 3,094, 2,989, 1,777, 1,725, 1,650, 1,447, 1,393, 1,314, 1,271, 1,183, 1,115, 1,090, 1,047, 998, 939, 847, 793, 765, 703, 632 cm$^{-1}$; PM: 182.18; MS m/z 183 (M$^+$); calculated elementary analysis C (59.34%), H (5.53%), found C (59.28%), H (5.68%). Example 3

Ethyl Cyclopenten-2-yl malonate Synthesis

Ethyl Malonic Acid Synthesis

Step 1

In a 250 ml three neck balloon provided with an addition bulb and a refrigerant, diethyl malonate is solubilized (20.00 g; 124.87 mmols) in (commercially available) ethanol. The resulting colourless mixture is stirred at room temperature and a KOH solution (7.00 g; 124.76 mmols) in ethanol (80 ml) is slowly added (addition time: 1 hr). After complete addition, the resulting mixture is stirred at room temperature overnight (ethyl potassium malonate precipitation). The salt precipitation is advantageously accelerated by cooling the reaction balloon in an ice bath. The potassium salt is recovered through filtration, washed with small ether quantities, then dried under reduced pressure (17.77 g; 84%)

Step 2

In a 250 ml three neck balloon provided with a magnetic stirrer, an addition bulb and a thermometer, the ethyl potassium malonate (17.77 g; 104.49 mmols) is solubilized in 18 ml water. The reaction mixture is cooled by means of an ice bath and 8, 2 ml concentrated hydrochloric acid are slowly added. The reaction mixture is filtered and the KCl precipitate is washed with ether (3×50 ml). The filtrate is allowed to settle and the aqueous phase is extracted with ether (3×50 ml). The combined ether phases are dried on anhydrous MgSO$_4$, filtered and concentrated to give the ethyl malonic acid (13.45 g; 82% global yield for both steps) in the form of a colourless oil.

Ethyl Cyclopenten-2-yl malonate Synthesis

To a 2-cyclopentenol solution (0.70 g; 8.32 mmols) in 30 ml dichloromethane are successively added ethyl malonic acid (0.85 g; 6,40 mmols.) and DMAP (0.08g; 0.64 mmol). The reaction mixture is stirred under inert atmosphere and cooled down to 0° C. At this temperature, DCC (1.39 g; 6.72 mmols) is added in one single portion. A milky white mixture is obtained, which is stirred at 0° C. for 1 hour, followed by room temperature until complete reaction (reaction evolution monitoring by TLC, eluent pentane/ethyl acetate: 8/2). The precipitate is filtered out on celite and washed with dichloromethane. The filtrate is washed with a NaHCO$_3$ (10 ml) saturated aqueous solution. The phases are separated and the aqueous phase is extracted with dichloromethane (3×10 ml). The combined organic phases are successively washed with a NaCl saturated aqueous solution and water, then dried on anhydrous MgSO$_4$ and concentrated. The precipitate is again filtered out on celite and washed with pentane. The purification of the reaction raw product is performed by silica column chromatography (elution pentane/ethyl acetate: 8/2) to give the compound of the invention (MRC2P45) (1.39 g; 84%) in the form of a colourless oil.

Product Characterization $^1$H NMR (CDCl$_3$, 400 MHz)δ: 1.28 (t, J=7.3 Hz, 3H), 1.83 (m, 1H), 2.31 (m, 2H), 2.50 (m, 1H), 3.34 (s, 1H), 4.20 (q, J=7.3 Hz, 2H), 5.76 (m, 1H), 5.83 (m, 1H), 6.13 (m, 1H); $^{13}$C NMR (CDCl$_3$, 175 MHz)δ: 13.41, 29.00, 30.47, 41.10, 60.64, 81.07, 128.46, 165.87, 165.94; IR (film): 3,451, 2,983, 1,750, 1,731, 1,459, 1,412, 1,370, 1,346, 1,323, 1,271, 1,189, 1,151, 1,032, 971, 917, 879, 736 cm$^{-1}$; PM: 198.22; MS m/z 170 (M$^+$–28).

Example 4

Methyl Cyclopenten-2-yl malonate Synthesis
Methyl Malonic Acid Synthesis
Step 1

In a 100 ml three neck balloon provided with an addition bulb and a refrigerant, dimethyl malonate is solubilized (10.00 g; 75.69 mmols) in 40 ml (commercially available) methanol. The resulting colourless mixture is stirred at room temperature and a KOH solution (4.25 g; 75.69 mmols) in methanol (40 ml) is slowly added (addition time: 1 hr). After complete addition, the resulting mixture is stirred at room temperature overnight (methyl potassium malonate precipitation). The salt precipitation can be accelerated by cooling the reaction balloon in an ice bath. The potassium salt is recovered through filtration, washed with small ether quantities, then dried under reduced pressure (10.27 g; 87%).
Step 2

In a 50 ml three neck balloon provided with a magnetic stirrer, an addition bulb and a thermometer, methyl potassium malonate (10.27 g; 65.76 mmols) is solubilized in 10 ml water. The reaction mixture is cooled by means of an ice bath and 5.5 ml concentrated hydrochloric acid are slowly added. The reaction mixture is filtered and the KCl precipitate is washed with ether (3×10 ml). The filtrate is allowed to settle and the aqueous phase is extracted with ether (3×10 ml). The combined ether phases are dried on anhydrous MgSO$_4$, filtered and concentrated to give the methyl malonic acid (7.42 g; 96%) in the form of a colourless oil.
Methyl cyclopenten-2-yl malonate Synthesis To a 2-cyclopentenol solution (1.00 g; 11.89 mmols) in 35 ml dichloromethane are successively added methyl malonic acid (1.08 g; 9.15 mmols) and DMAP (0.11 g; 0.91 mmols). The reaction mixture is stirred under inert atmosphere and cooled down to 0° C. At this temperature, DCC (1.98 g; 9.60 mmols) is added in one single portion. A milky white mixture is obtained, which is stirred at 0° C. for 1 hour, followed by room temperature until complete reaction (reaction evolution monitoring by TLC, eluant pentane/ethyl acetate: 8/2). The precipitate is filtered out on celite and washed with dichloromethane. The filtrate is washed with a NaHCO$_3$ (10 ml) saturated aqueous solution. The phases are separated and the aqueous phase is extracted with dichloromethane (3×10 ml). The combined organic phases are successively washed using a NaCl saturated aqueous solution and water, then dried on anhydrous MgSO$_4$ and concentrated. The precipitate is again filtered out on celite and washed with pentane. The purification of the reaction raw product is performed through silica column chromatography (elution pentane/ethyl acetate: 8/2) to give the compound of the invention (MCR2P85) (1.40 g; 83%) in the form of a colourless oil.
Product Characterization $^1$H NMR (CDCl$_3$, 400 MHz)δ: 1.85 (m, 1H), 2.29 (m, 2H), 2.51 (m, 1H), 3.36 (S, 2H), 3.75 (s, 3H), 5.76 (m, 1H), 5.83 (m, 1H), 6.13 (m, 1H); $^{13}$C NMR (CDCl$_3$, 175 MHz)δ: 29.27, 30.73, 41.16, 52.04, 81.43, 128.44, 137.83, 166.10, 166.74; IR (film): 2,955, 2,858, 1,736 1,438, 1,412, 1,348, 1,273, 1,152, 1,028, 968, 917, 878, 737 cm$^{-1}$; PM: 184.19; MS m/z 156 (M$^+$–28); calculated elementary analysis C (58.69%), H (6.57%), found C (58.60%), H (6.59%).

Example 5

N-N'-diphenyl malonamide Synthesis

To a N-phenylamine solution (0.75 ml; 8.22 mmols) in 25 ml dichloromethane is added triethylamine (0.72 ml; 5.14 mmols). The resulting colourless mixture is cooled down to 0° C., using an ice bath and malonyl dichloride (0.5 ml; 5.14 mmols) is slowly added to through a syringe. A vivid red/orange solution accompanied with a precipitate is obtained. The reaction mixture is stirred at 0° C. for 2 hours (reaction evolution monitoring by TLC, eluent pentane/ethyl acetate: 1/9), followed by the addition of approximately 4 ml of a 10 HCl solution. The phases are separated and the organic phase is successively washed with water (10 ml) and with a NaCl (10 ml) saturated aqueous solution. After being dried on anhydrous MgSO$_4$, filtered and concentrated, an orange-coloured solid is isolated. The purification is performed by recrystallization in a pentane/ethyl acetate blend in order to give the compound of the invention (MCR2P219) (0.33 g; 32%) in the form of an ecru-coloured powder.
Product Characterization $^1$H NMR (DMSO-d$_6$, 400 MHz)δ: 3.47 (s, 2H), 7.06 (m, 2×1H), 7.31 (m, 2×2H), 7.60 (m, 2×2H), 10.17 (s, 2H); $^{13}$C NMR (DMSO-d$_6$, 175 MHz)δ: 37.20, 110.30, 114.60, 120.00, 130.20, 156.60; IR (KBr tablets): 3,274, 3,152, 3,066, 1,669, 1,650, 1,599, 1,560, 1,538, 1,500, 1,444, 1,416, 1,358, 1,309, 1,294, 1,251, 1,193, 1,162, 979, 905, 857, 752, 693, 618 cm$^{-1}$; P.F.=220° C.; PM 254.29.

Example 6

Ethyl N-phenylamido Ethanoate Synthesis
Ethyl Chloroformyl Ethanoate Synthesis

In a 50 ml three neck balloon provided with an addition bulb, a thermometer and a refrigerant, ethyl malonic acid is introduced (1.00 g; 7.57 mmols) in 8 ml drydichloromethane. The balloon is cooled down to 0° C. using an ice bath. At this temperature, 1.5 thionyl chloride equivalents (0.83 ml;. 11.35 mmols) diluted in 5 ml dichloromethane are slowly added. After complete addition, the reaction mixture is stirred at 0° C. for 10 minutes, subsequently brought to reflux for 2 hours. After concentration, the ethyl chloroformyl ethanoate (0.99 g; 87%) is isolated and used with no additional purification in the next step.
Product Characterization $^1$H RMN (CDCl$_3$, 400 MHz)δ: 1.31 (t, J=7.3 Hz, 3H), 3.87 (s, 2H), 4.26 (q, J=7.3 Hz, 2H); IR (film): 2,989, 1,802, 1,742, 1,577, 1,468, 1,401, 1,372, 1,323, 1,260, 1,164, 1,035, 982, 940, 859, 652, 612 cm$^{-1}$; PM: 150.56.
Ethyl N-phenylamido Ethanoate Synthesis To a N-phenylamine solution (0.25 g; 0.24 ml, 2.66 mmols) in 15 ml dry dichloromethane, are added 1.25 triethylamine equivalents (0.46 ml; 3.32 mmoles). The resulting solution is cooled down to 0° C. using an ice bath. At this temperature, 1.25 ethyl chloroformyl ethanoate equivalents (0.43 ml; 3.32 mmols) are slowly added through a syringe. A vivid orange solution is obtained, which is stirred at 0° C. overnight (reaction evolution monitoring by TLC) (eluent pentane/ethyl acetate: 1/9), followed by the addition of approximately 4 ml of a 10% HCl solution. Both phases are separated and the organic phase is washed with water. The combined aqueous phases are extracted with dichloromethane. The organic phases are washed with a NaCl saturated aqueous solution, dried on anhydrous $MgSO_4$, filtered and concentrated. The purification is performed through silica column chromatography (eluent pentane/ethyl acetate: 1/9) to give quantitatively the compound of the invention (MCR2P231) (0.55 g; 100%).
Product Characterization $^1H$ NMR ($CDCl_3$, 400 MHz)δ: 1.32 (t, J=7.3 Hz, 3H), 3.47 (s, 2H), 4.26 (q, J=7.3 Hz, 2H), 7.12 (t, J=7.3 Hz, 1H), 7.33 (t, J=7.8 Hz, 2H), 7.55 (d, J=7.8 Hz, 2H); $^{13}C$ NMR ($CDCl_3$, 175 MHz)δ: 13.67, 42.26, 61.38, 119.98, 124.25, 128.55, 137.37, 163.77, 168.70; IR (film): 3,313, 3,143, 2,985, 1,738, 1,668, 1,603, 1,549, 1,500, 1,445, 1,372, 1,342, 1,244, 1,190, 1,156, 1,033, 906, 844, 757, 695 $cm^{-1}$; PM: 207,23; MS m/z 207 ($M^+$).

Example 7

Ethyl 2,6-dimethyl-N-phenylamido Ethanoate Synthesis

To a 2,6-dimethyl-N-phenylamine solution (1.31 ml; 10.63 mmols) in 60 ml dry dichloromethane is added triethylamine (1.85 ml; 13.28 mmols). The resulting colourless mixture is cooled down to 0° C. through an ice bath and ethyl chloroformyl ethanoate (1.3 ml; 10.15 mmols) is then slowly added through a syringe. A vivid red/orange solution is obtained, which is maintained under stirring at 0° C. overnight (reaction evolution monitoring by TLC, eluent pentane/ethyl acetate: 1/9), followed by the addition of approximately 4 ml of a 10% HCl solution. Both phases are separated and the organic phase is washed with water (3×10 ml). The combined aqueous phases are extracted with dichloromethane. The organic phase is washed with a NaCl saturated aqueous solution, then dried on anhydrous $MgSO_4$. After being filtered and concentrated, the raw ester amide is obtained in the form of an orange-coloured solid. The purification is performed by recrystallization in a pentane/ethyl acetate blend in order to give thee compound of the invention (MCR2P255) (1.67 g; 67%) in the form of an ecru-coloured powder.
Product Characterization
$^1H$ NMR ($CDCl_3$, 400 MHz)δ: 1.35 (t, J=7.3 Hz, 3H), 2.20 (s, 6H), 3.50 (s, 2H), 4.25 (q, J=7.3 Hz, 2H), 7.10 (m, 3H), 8.55 (broadened s, 1H); $^{13}C$ NMR ($CDCl_3$, 175 MHz) δ: 13.98, 18.29, 41.20, 61.67, 127.23, 128.06, 133.50, 135.10, 163.38, 169.66; IR (KBr tablet): 3,226, 3,031, 1,731, 1,666, 1,642, 1,595, 1,536, 1,477, 1,411, 1,397, 1,370, 1,351, 1,264, 1,218, 1,204, 1,166, 1,030, 986, 880, 761, 723, 635 $cm^{-1}$; P.F.=103° C.; PM: 235.28; MS m/z 235 ($M^+$)

Example 8

Ethyl N-methyl-N-cyclohexamido Ethanoate Synthesis

To a N-methyl N-cyclohexylamine solution (0.41 ml; 3.12 mmols) in 20 ml dry dichloromethane is added triethylamine (0.54 ml; 3.91 mmols). The resulting colourless mixture is cooled down to 0° C. through an ice bath and then ethyl chloroformyl ethanoate (0.5 ml; 3.91 mmols) is slowly added through a syringe. A vivid red/orange solution is obtained which is maintained under stirring at 0° C. for 4 hours (reaction evolution monitoring by TLC, eluent pentane/ethyl acetate: 1/9), followed by the addition of approximately 4 ml of a 10% HCl solution. Both phases are separated and the organic phase is washed with water (3×10 ml). The combined aqueous phases are extracted with dichloromethane. The organic phase is washed with a NaCl saturated aqueous solution, followed by drying on anhydrous $MgSO_4$. After being filtered and concentrated, the raw ester amide is obtained. The purification is performed through silica column chromatography (eluent pentane/ethyl acetate: 1/9) to give the compound of the invention (MCR2P237) (0.71 g; 100%) in the form of an orange liquid.
Characterization of the Resulting Product
$^1H$ NMR ($CDCl_3$, 400 MHz)δ: 1.27–1.67 (m, 14H), 2.84 (s, 3H) 3.44 (s, 1H), 3.47 (s, 1H), 4.21 (q, J=7.3 Hz, 2H), 4.40 (m, enol form contribution); $^{13}C$ NMR ($CDCl_3$, 175 MHz)δ: 14.52, 24.99, 29.05, 30.14, 41.44, 52.09, 60.48, 65.10, 165.13, 167.06; IR (film) 2,933, 2,858, 1,741, 1,645, 1,477, 1,450, 1,408, 1,370, 1,326, 1,254, 1,164, 1,098, 1,035, 947, 895, 847, 788, 674 $cm^{-1}$; PM: 227.30.

Example 9

S,S dicyclopenten-2-yl Malonate Enantiomer Synthesis

2-Bromo-2-cyclopentenone Synthesis

In a 250 ml three neck balloon provided with an addition bulb and a refrigerant, 2-cyclopentenone is solubilized (7.24 g; 88.2 mmole) in 60 ml $CCl_4$. The solution is cooled down to 0° C. and a $Br_2$ solution (15.51 g; 97 mmols) in the $CCl_4$ is added dropwise. After complete addition, a $N-Et_3$ solution (13.39 g; 132 mmols) in the $CCl_4$ (60 ml) is added at the same temperature dropwise. The resulting mixture is stirred at room temperature for 2 hours, then filtered. The filtrate is successively washed with HCl 1M, 10% $NaHCO_3$ and $H_2O$. The organic phase is dried on anhydrous $MgSO_4$, filtered and concentrated. The thereby obtained solid is recrystallized (cyclohexane/$Et_2O$) to give the 2-bromo-2-cyclopentenone (7.5 g; 53%) in the form of a white solid.
(±)-2-bromo-2-cyclopentenol Synthesis To a 2-bromo-2-cyclopentenone solution (8 g; 49.7 mmols) in methanol (150 ml) is added heptahydrate cerium chloride ($CeCl_3.7H_2O$) (20.36 g; 54.7 mmols) and the reaction mixture is stirred at room temperature for 40 minutes. The mixture is then cooled down to 0° C. and sodium borohydride ($NaBH_4$) (2.07 g; 54.7 mmoles) is slowly added. After complete addition, the mixture is stirred at 0° C. for 2 hours. A $NH_4Cl$ aqueous solution is then added. The phases are separated and the aqueous phase is extracted several times with ether (5×50 ml). The combined organic phases are dried on anhydrous $MgSO_4$ and concentrated. The raw product thereby obtained is purified with silica chromatography (elution pentane/ethyl acetate: 9/1) to give the (±)-2-bromo-2-cyclopentenol (6.0 g; 74%) in the form of a yellow oil.
Product Characterization
$^1H$ NMR ($CDCl_3$, 400 MHz) 1.85–2.04 (m, 2H), 2.20–2.60 (m, 3H), 4.71 (b, 1H), 6.05–6.08 (m, 1H)
(S)-2-bromo-2-cyclopentenol Synthesis To a (±)-2-bromo-2-cyclopentenol solution (6.00 g; 36.8 mmols) in a mixture of isopropenylacetate (24 ml) and cyclohexane (96 ml) is added the Novozym Lipase enzyme 435 (1,5 g). The mixture is stirred for 1 hour at room temperature, then filtered. The filtrate is evaporated and the thereby obtained residue is purified through silica chromatography (elution cyclohexane/AcOEt: 9/1) to give the (S)-2-bromo-2-cyclopentenol (1.5 g; 50%) in the form of a white solid.
Product Characterization
$^1H$ NMR ($CDCl_3$, 400 MHz)δ: 1.85–2.04 (m, 2H), 2.20–2.60 (m, 3H), 4.71,(b, 1H), 6.05–6.08 (m, 1H). $[\alpha]^{22}D=-47.5°$ (c=1.0, $CHCl_3$)
(S)-2-cyclopentenol Synthesis In a 50 ml three neck balloon provided with an addition bulb, a thermometer and a refrigerant, tBuLi (solution in pentane 1.7M; 23 ml; 39.1 mmols) and $Et_2O$ (10 ml) are introduced. The mixture is then cooled down to $-78°$ C. and (S)-2-bromo-2-cyclopentenol (1.90 g; 11.7 mmols) in solution in $Et_2O$ (15 ml) is slowly added. After complete addition, the mixture is allowed to heat at $0°$ C. and is stirred at this temperature for 2 hours. A diluted $NH_4Cl$ solution in water is then slowly added. The organic phase is separated and the aqueous phase extracted several times using $Et_2O$. The combined organic phases are dried on anhydrous $MgSO_4$, and concentrated to give the (S)-2-cyclopentenol in the form of oil (600 mg; 61%).

Product Characterization $^1H$ NMR $(CDCl_3, 400$ MHz$)\delta$: 1.65–1.73 (m, 2H), 2.22–2.32 (m, 2H), 2.48–2.56 (m, 1H), 4.87 (b, 1H), 5.81–5.89 (m, 1H), 5.90–6.10 (m, 1H) $[\alpha]^{22}D$ $-119.2°$ (c=1,0, $CHCl_3$)

Di-(S)-2-cyclopenten-2-yl Malonate Synthesis

The synthesis of di-(S)-2-cyclopenten-2-yl malonate is performed using the same protocol as described in example 1.

Product Characterization $^1H$ NMR $(CDCl_3, 400$ MHz$)\delta$:: 1.80–1.92 (m, 2H), 2.20–2.40 (m, 4H), 2.45–2.60 (m, 2H), 3.34 (s, 2H), 5.75–7.79 (m, 2H), 5.83–5.86 (m, 2H), 6.10–6.17 (m, 2H) $[\alpha]^{22}D=212.8°$ (c=0,97, $CHCl_3$)

Example 10

In vitro Tests

Effect of the Products at the Mitochondrial Respiration Level (Effect at the Level of Stages III and IV and at the RCR Level The compounds of the invention are characterized by the inhibition of the reduction of the ATP content, the activation of the A2 phospholipase and the neutrophilic polymorphonuclear adherence (PMN) on the cultured endothelial cells of the human umbilical vein when they are incubated in hypoxic conditions.

The inhibition by the compounds of the invention of the activation cascade of endothelial cells induced by hypoxia and the ATP content preservation in the endothelial cells under hypoxic conditions are obtained by the compounds of the invention that hold the mitochondrial respiratory activity. This is confirmed by measuring the respiratory activity expressed by the respiratory control (RCR) of rat liver mitochondria treated per os. The mitochondria are isolated according to the method described by Nowicki et al., *J. of Cerebral Blood Flow and Metabolism* 2, p. 33–40 (1982). The mitochondrial respiration is measured by an oxygen electrode connected to a recorder. The RCR represents the respiratory control, and represents the ratio of the oxygen consumption in the presence of an endogenous substrate (glutamate/malate) to the consumption after ADP phosphorylation in ATP. This technique has been described by Chance & William (*Nature* 175, p. 1120–1121 (1955)).

Several compounds of the invention have been tested at various concentrations on the respiratory activity of purified mitochondria obtained from rat livers. The mitochondria have been preincubated in the presence of the compounds so as to measure the slope in respiration stages III and IV, as described in WO98/51291. The RCR has been subsequently calculated.

The results hereafter show that the products of example 1 and example 2 have an action on the RCR with a maximum effect at $10^{-7}$ mol/l for the example 2 product. This RCR increase is mainly due to a decrease effect of respiration stage IV.

The compound of example 1 significatively increases the mitochondria RCR, namely because this molecule strongly decreases respiration stage IV. The effect is optimal at $10^{-6}$ mol/l and decreases with the concentration to become negligible at $10^{-9}$ mol/l.

The table below summarizes the effect of other compounds of the invention with the optimum concentrations at which the effects have been observed.

TABLE I

| Compound | RCR increase (*) | Concentration |
|---|---|---|
| Ethyl cyclopenten-2-yl malonate | 10% | $10^{-5}$ M |
| Methyl cyclopenten-2-yl malonate | 15% | $10^{-6}$ M |
| di-(S)-cyclopenten-2-yl malonate | 18% | $10^{-6}$ M |
| N,N'-diphenylmalonamide | 5% | $10^{-7}$ M |
| Ethyl N-phenlyamido ethanoate | 6.6% | $10^{-6}$ M |
| Ethyl 2,6-dimethyl-N-phenylamido ethanoate | 13% | $10^{-6}$ M |
| Ethyl N-methyl-N-cyclohexamido ethanoate | 15% | $10^{-7}$ M |

(*) In % relative to the control brought to 100%

The results show that the compounds of the invention are able to protect reproducibly the decrease in ATP content induced by hypoxia in the endothelial cells. The 92.5% average maximum protection is observed at $10^{-4}$ mol/l concentration for the example 2 compound. This protection decreases with this compound concentration to become negligible at $10^{-6}$ mol/l. The results also show that the compound from example 1 is able to protect reproducibly the decrease in ATP content induced by hypoxia in the endothelial cells. The 92.1% average maximum protection is observed at $10^{-4}$ mol/l to $10^{-5}$ mol/l concentration. This protection decreases with this compound concentration to become negligible at $10^{-8}$ mol/l.

This protection is reproducible as long as the same curve evolutions are always found for all the experiments, and even if there is a variability between experiments at the level of the hypoxia effect on the ATP content. This variability is inherent to the experimental model. Indeed, for each experiment, a different culture is used from different umbilical cord isolated cells and there is a behaviour variability of the cells from one cord to another.

Example 11

Stability in Human Plasma

The compounds of examples 1 and 2 have been submitted to stability tests in order to evaluate their behaviour when in contact with plasma after a 3 and 24 hour incubation at a temperature of $37°$ C. These tests have been performed using GC following the evolution of chromatograms of the different esters compared to an internal standard as a function of time.

The injection of GC/MF pure products has been performed in the following conditions:

injection temperature: $250°$ C.

initial temperature: $40°$ C.

final temperature: $250°$ C.

temperature gradient: $10°$ C./mn injection method: split retention time: compound of example 1: 13.39 compound of example 2: 11.23.

The different compounds have been prepared as follows: 10 µl of pure compound have been dissolved in 100 µl plasma at a temperature of 37° C. The resulting solution is stirred. After a 3 or 24 hour period of time, 5 μl of internal standard (N-benzylamine) and 1 ml ether are added to the solution maintained at 37° C. The sample is centrifuged for 10 minutes at a rate of 13,000 rpm. 1 μl of the supernatant phase (ether phase) is injected in GC. The sample is then GC analyzed. The chromatogram analysis allows to emphasize that after 3 hours in contact with human plasma maintained at 37° C., the peak corresponding to the compounds of the invention is still observed. The compounds of the invention do not therefore undergo or undergo little significant degradations after 3 hours in the presence of plasma. No other peak optionally corresponding to metabolization products is observed. After 24 hours in contact with human plasma, the presence of the peak corresponding to the compound of example 1 is still observed. However, the peaks corresponding to the compound of example 2 are not found any more.

Example 12

In vitro Effect on the Neutrophil Adherence to the Endothelial Cells being Incubated under Hypoxia Endothelial cells have been incubated under hypoxia in the presence of different concentrations of the compounds of the invention. After incubation, the cells are co-incubated with a non stimulated human neutrophil suspension. In normoxic conditions, the neutrophil adherence to the endothelial cells is low (from 5 to 10%), but it increases by about 3times under hypoxia.

The effect of the compound of example 1 on the neutrophil adherence to the endothelial cells being incubated under hypoxia is characterized by an inhibition of the hypoxia induced adherence, and this depending on the concentration between $10^{-5}$ mol/l and $10^{-8}$ mol/l. An activity optimum should be obtained between $10^{-7}$ mol/l and $10^{-5}$ mol/l. Similarly, the compound of the example 2 inhibits the hypoxia induced neutrophil adherence increase between $10^{-6}$ mol/l and $10^{-8}$ mol/l with a 71% maximum at $10^{-8}$ mol/l.

Example 13

In vivo Effect on Liver After Treatment of Rats Per os for 5 Days

The rats have been treated per os either with solutions having an increasing concentration of each of the compounds of the invention or with DMSO-containing batches at the same concentration as that used for dissolving the molecules (control rats) at the rate of once a day for 5 days.

Following the treatment, the rats are sacrificed. The mitochondria are isolated from the liver and their respiratory activity is measured every 15 minutes for the 75 minutes following the isolation procedure.

The optimal concentration in pre-incubation for the compound of the example 1 is $10^{-6}$ mol/l (0.236 μg/l). The dosis used to treat the rats is therefore 2.36 mg/kg and 5 times inferior and 5 times higher and 20 times higher doses have also been tested.

For the compound of the example 2, the optimal concentration in pre-incubation is $10^{-7}$ mol/l (0.0183 μg/ml). The tested doses are therefore 0.18 mg/kg. As such dose is weakly active, 5 and 20 times higher doses have also been tested.

The compound of the example 1 increases in a dose dependent and significative way the hepatic mitochondria RCR after a 5 day treatment with a 25% increase at 2.36 mg/kg. At a higher dosis, the molecule becomes weakly toxic and the RCR falls slightly below the control values. Such a RCR increase is due to a clear decrease of respiration stage IV.

The compound of the example 2 increases in a dose dependent and significative way the mitochondria RCR with a 17% maximum at 3.6 mg/kg. This RCR increase is also due to a decrease of respiration stage IV.

Example 14

In vivo Effect on the Heart After Treatment of Rats Per os for One Day

The rats have been treated per os with the 2.36 mg/kg concentrations of the compound of the example 1 or with the 3.6 mg/kg concentrations of the compound of the example 2, either with DMSO-containing batches at the same concentration as that used for dissolving the molecules (control rats) at the rate of once.

The following day, the rats are sacrificed and their mitochondria are isolated from the heart. Their respiratory activity is measured every 15 minutes for the 75 minutes following the isolation procedure.

The compound of the example 1 increases the heart mitochondria RCR after a one-day treatment with a 41% increase at 2.36 mg/kg. The compound of the example 2 increases the mitochondria RCR after a one day treatment with a 56% increase at 3.6 mg/kg. Example 15

In vitro Application for the Apoptosis Treatment

Promyelocyte cells are incubated in the presence of apoptosis-inducing agents like the etoposide, a type II topoisomerase inhibitor. After incubation, different parameters indicative of the apoptosis are detectable: caspase activation, cytochrome C release by the mitochondria, DNA fragmentation, etc.

Unexpectedly, if the cells are incubated in the presence of etoposide and in the presence of the compound of the example 1, an apoptosis induction inhibition is observed. Such an inhibition is a function of the dosis between $10^{-5}$ mol/l and $10^{-8}$ mol/l. Thus, caspase 3 activation, cytochrome C release by the mitochondria and DNA fragmentation are inhibited.

What is claimed is:

1. A compound of formula I, a salt or a prodrug thereof corresponding to formula I:

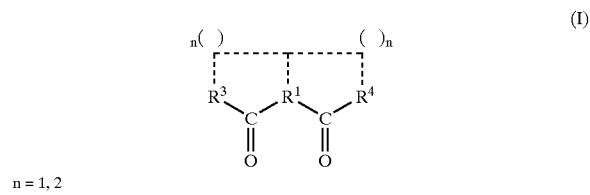

n = 1, 2 wherein:

R$^1$ is selected from the group consisting of CH$_2$, NH, and a group wherein said group together with R$^3$ and/or R$^4$ forms an aromatic or non-aromatic ring having 5 or 6 carbon atoms, optionally comprising on each ring an heteroatom, preferably a nitrogen, oxygen or sulfur atom, $R^3$ and/or $R^4$ represent:

an amine having the formula:

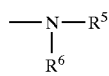

or a group having the formula $—Z—R^6$ wherein:
Z represents O or S,
$R^5$ represents H or an alkyl group with 1 to 6 carbon atoms,
$R^6$ represents a hydrophobic group, preferably a terbutyl, an allyl or an aromatic or non-aromatic ring having 5, 6 or 7 carbon atoms optionally comprising one or several heteroatoms and wherein the carbon atoms are optionally substituted for by:
an alkyl group $R^7$ having 1 to 6 carbon,
a ketone group,
a hydroxyl group,
an ester group,
a halogen element (F, Cl, Br or I),
a trifluoromethyl group ($CF_3$), or
a group having the formula:

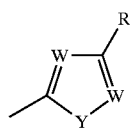 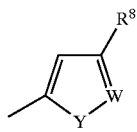 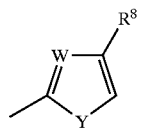

wherein:
W represents CH or a nitrogen atom,
Y represents S or O, and
$R^8$ represents an alkyl group having 1 to 6 carbon atoms, preferably a methyl or ethyl group,
with the additional condition that, if $R^3$ together with $R^1$ forms said above-mentioned ring or if $R^3$ is either an amine of formula:

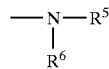

or the above-mentioned group of formula $—Z—R^6$, $R^4$ represents an alkyl group having 1 to 10 carbon atoms, either saturated or unsaturated, optionally comprising one or more heteroatoms.

2. A compound according to claim 1, characterized in that $R^5$, $R^7$ and $R^8$ represent H or a methyl group, and wherein $R^1$ is $CH_2$.

3. A compound according to claim 1, wherein $R^1$ is $CH_2$ and in that $R^3$ and $R^4$ represent an amine having the formula:

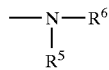

or a group having the formula: $—O—R^6$, wherein $R^6$ represents a terbutyl, a cyclopentene, a cyclohexane or a benzene group the carbon atoms of which are optionally substituted for by a methyl group, a ketone group, a hydroxyl group, an ester group, a halogen element or a trifluoromethyl group ($CF_3$).

4. A compound according to claim 1, wherein it is selected from the group consisting of dicyclopenten-2-yl malonate, 2-propenyl 3-oxa-2-oxobicylo[3.1.0]hexane-1-carboxylate, ethyl cyclopenten-2-yl malonate, di-(S)-cyclopenten-2-yl malonate, methyl cyclopenten-2-yl malonate, N,N'-diphenyl malonamide, ethyl N-phenylamido ethanoate, ethyl 2,6-dimethyl-N-phenylamido ethanoate and ethyl N-methyl-N-cyclohexylamido ethanoate, optionally their salts or pro-drugs thereof.

5. A pharmaceutical composition comprising an appropriate pharmaceutical carrier and one or more compounds according to claim 1.

6. Method for preparing the compound according to claim 1, comprising the following steps:
esterification of a $R^3$—H formula intermediate compound by a group

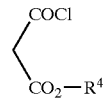

in the presence of dicyclohexyl carbodiimide (DCC),
optionally followed by one or more cyclizing reactions in the presence of an oxidizing agent.

7. A method for treating and/or preventing ischemia, pathologies associated with ischemia or pathologies associated with mitochondrial deficiencies, comprising administering a compound according to claim 1 to a mammal.

8. A compound according to claim 2, wherein $R^1$ is $CH_2$ and in that $R^3$ and $R^4$ represent an amine having the formula:

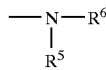

or a group having the formula: $—O—R^6$, wherein $R^6$ represents a terbutyl, a cyclopentene, a cyclohexane or a benzene group the carbon atoms of which are optionally substituted for by a methyl group, a ketone group, a hydroxyl group, an ester group, a halogen element or a trifluoromethyl group ($CF_3$).

9. A pharmaceutical composition comprising an appropriate pharmaceutical carrier and one or more compounds according to claim 2.

10. A pharmaceutical composition comprising an appropriate pharmaceutical carrier and one or more compounds according to claim 3.

11. A pharmaceutical composition comprising an appropriate pharmaceutical carrier and one or more compounds according to claim 4.

12. A method for treating and/or preventing ischemia, pathologies associated with ischemia or pathologies associated with mitochondrial deficiencies, comprising administering a compound according to claim 2 to a mammal.

13. A method for treating and/or preventing ischemia, pathologies associated with ischemia or pathologies associated with mitochondrial deficiencies, comprising administering a compound according to claim 3 to a mammal.

14. A method for treating and/or preventing ischemia, pathologies associated with ischemia or pathologies associated with mitochondrial deficiencies, comprising administering a compound according to claim 4 to a mammal.

15. A method for treating and/or preventing ischemia, pathologies associated with ischemia or pathologies associated with mitochondrial deficiencies, comprising administering a pharmaceutical composition according to claim 5 to a mammal.

16. The compound of claim 1, wherein the group comprises a carbon atom.

17. The compound of claim 1, wherein $R^5$ is a methyl group or ethyl group.

18. The compound of claim 1, wherein $R^7$ is a methyl group or ethyl group.

* * * * *